United States Patent
Stegall et al.

(10) Patent No.: US 11,918,439 B2
(45) Date of Patent: Mar. 5, 2024

(54) PROJECTED TEXTURE PATTERN FOR INTRA-ORAL 3D IMAGING

(71) Applicant: MEDIT CORP., Seoul (KR)

(72) Inventors: David B. Stegall, Saint Paul, MN (US); Shannon D. Scott, Hudson, WI (US); Amanda L. Kastanek, Saint Paul, MN (US)

(73) Assignee: MEDIT CORP., Seoul (KR)

( * ) Notice: Subject to any disclaimer, the term of this patent is extended or adjusted under 35 U.S.C. 154(b) by 823 days.

(21) Appl. No.: 16/977,365

(22) PCT Filed: Feb. 7, 2019

(86) PCT No.: PCT/IB2019/050996
§ 371 (c)(1),
(2) Date: Sep. 1, 2020

(87) PCT Pub. No.: WO2019/155401
PCT Pub. Date: Aug. 15, 2019

(65) Prior Publication Data
US 2021/0361395 A1    Nov. 25, 2021

Related U.S. Application Data

(60) Provisional application No. 62/629,244, filed on Feb. 12, 2018.

(51) Int. Cl.
*G06T 7/00* (2017.01)
*A61C 9/00* (2006.01)
(Continued)

(52) U.S. Cl.
CPC ............ *A61C 9/006* (2013.01); *G01B 11/254* (2013.01); *G02B 5/3083* (2013.01);
(Continued)

(58) Field of Classification Search
CPC .... A61C 9/006; G01B 11/254; G02B 5/3083; G06T 7/0012; G06T 7/40;
(Continued)

(56) References Cited

U.S. PATENT DOCUMENTS

| 9,591,286 B2 | 3/2017 | Yun et al. |
| 2007/0047079 A1 | 3/2007 | Trissel |

(Continued)

FOREIGN PATENT DOCUMENTS

EP    2078493 B1    5/2015

OTHER PUBLICATIONS

International Search Report and Written Opinion dated Jun. 7, 2019, for International Application No. PCT/IB2019/050996, 9 pages.

*Primary Examiner* — Ming Y Hon
(74) *Attorney, Agent, or Firm* — Sughrue Mion, PLLC

(57) ABSTRACT

Apparatus for powder-free intra-oral 3D imaging by using a projected texture pattern. A projector projects a random texture pattern of light to teeth to be imaged, and a digital image sensor receives the projected texture pattern from the teeth. The reflected pattern of light reflects and scatters from the teeth. The texture pattern can be a grid having clusters of bright and dark blocks in a pseudo-random arrangement and can provide for powder-free intra-oral 3D imaging by using the pattern to optically simulate powder applied to the teeth. Polarizers can be used in the optical path to transmit the directly reflected light to the image sensor and suppress or discard some of the unwanted scattered light.

20 Claims, 5 Drawing Sheets

(51) Int. Cl.
*G01B 11/25* (2006.01)
*G02B 5/30* (2006.01)
*G02B 27/28* (2006.01)
*G06T 7/40* (2017.01)
*H04N 9/31* (2006.01)

(52) U.S. Cl.
CPC .......... *G02B 27/283* (2013.01); *G06T 7/0012* (2013.01); *G06T 7/40* (2013.01); *H04N 9/3167* (2013.01); *G06T 2207/30036* (2013.01)

(58) Field of Classification Search
CPC ........ G06T 2207/30036; H04N 9/3167; A61B 5/0062; A61B 5/0088
See application file for complete search history.

(56) References Cited

U.S. PATENT DOCUMENTS

| | | | |
|---|---|---|---|
| 2010/0268069 A1 | 10/2010 | Liang | |
| 2011/0285966 A1* | 11/2011 | Kamm | H04N 13/337 359/558 |
| 2015/0029321 A1* | 1/2015 | Imamura | G01N 21/59 348/136 |
| 2016/0231551 A1 | 8/2016 | Berner | |
| 2018/0025529 A1* | 1/2018 | Wu | G01J 3/508 345/426 |
| 2018/0299262 A1* | 10/2018 | Thiel | A61B 1/000095 |
| 2019/0212253 A1* | 7/2019 | Haider | G01N 21/21 |

\* cited by examiner

PROJECTED TEXTURE PATTERN FOR INTRA-ORAL 3D IMAGING

BACKGROUND

Some intra-oral scanners use conventional passive stereo vision where the teeth are uniformly illuminated and three cameras simultaneously capture images of the scene. As long as the object surfaces in the scene exhibit sufficient texture, the multiple-view images are processed to produce a three-dimensional (3D) map of the resolved features. In the case of teeth, the enamel is relatively translucent to visible light and scarcely exhibits any inherent texture. The computational processing consequently has difficulty generating 3D data from the poor quality images. To resolve this issue, the texture can be improved by applying powder to teeth. Even though only a sparse dusting of powder is sufficient to increase texture, the use of powder can be undesirable during the scanning of teeth to take a digital impression. Accordingly, a need exists for powder-free intra-oral scanning to generate a digital impression of teeth or other intra-oral structures.

SUMMARY

An apparatus of an embodiment for intra-oral imaging using a projected texture pattern includes a projector and an image sensor. The projector is configured to project a random texture pattern of light through to an object to be imaged, and the image sensor is configured to receive the projected texture pattern from the object.

An apparatus of another embodiment for intra-oral imaging using a projected texture pattern includes a projector, a beam splitter, and an image sensor. The beam-splitter is located between the projector and an object to be imaged. The projector is configured to project a random texture pattern of light through the beam-splitter, and the image sensor is configured to receive the projected texture pattern from the object and through the beam-splitter.

In both embodiments, the projected texture pattern is sufficient for the image sensor to resolve features on a surface of the object such that powder need not be applied to the object for desired imaging.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

By projecting a texture pattern onto teeth and optionally managing the polarization of the projection and imaging of the texture, 3D digital scanning of the teeth can be performed without the need for powder. If non-optimal texture is projected onto the teeth, sub-surface scattering of light will hinder the contrast captured by the camera. Regions that were intended to be dark within the projected texture will become back-lit by the sub-surface scattering of light from the bright regions of the projected pattern. In effect, the camera images will exhibit severe blurring and poor contrast of the projected texture for all but the coarsest patterns. In order to improve the contrast of a more finely projected texture, the sub-surface or global light can be suppressed to a sufficient level so as to improve the contrast seen in the direct light reflected from the surface of the tooth. By conditioning the projected texture to have a well-defined polarization state before reaching the tooth, the system can know a priori what the polarization state of the direct reflection from the tooth will be, whereas the global light will scramble any incident polarization state. By placing a polarizer in between the tooth and camera so that it is co-linear with the incident projected texture, the direct light will pass through the polarizer undisturbed but about half of the global light will be suppressed. In some cases, the projected texture pattern is sufficient for imaging, and polarizers are not needed.

Furthermore, a potentially useful byproduct of using projected texture for 3D digital mapping of teeth is the ability to characterize the scattering and absorption properties of the oral tissue. As illustrated for example in FIG. 5, the modulation transfer function of parameter S, which contributes to the image spatial frequency spectrum, is explicitly related to both the scattering and absorption coefficients of the tooth. The relationship is based on the diffusion approximation to the more rigorous radiant transfer equation. Such optical properties could prove clinically useful for diagnosing the health of teeth and soft tissue. These parameters could be calculated simultaneously with the 3D digital impression, such that a 3D rendering of the optical properties could be provided to the user, just as the 3D impression is shown.

Figure 1:
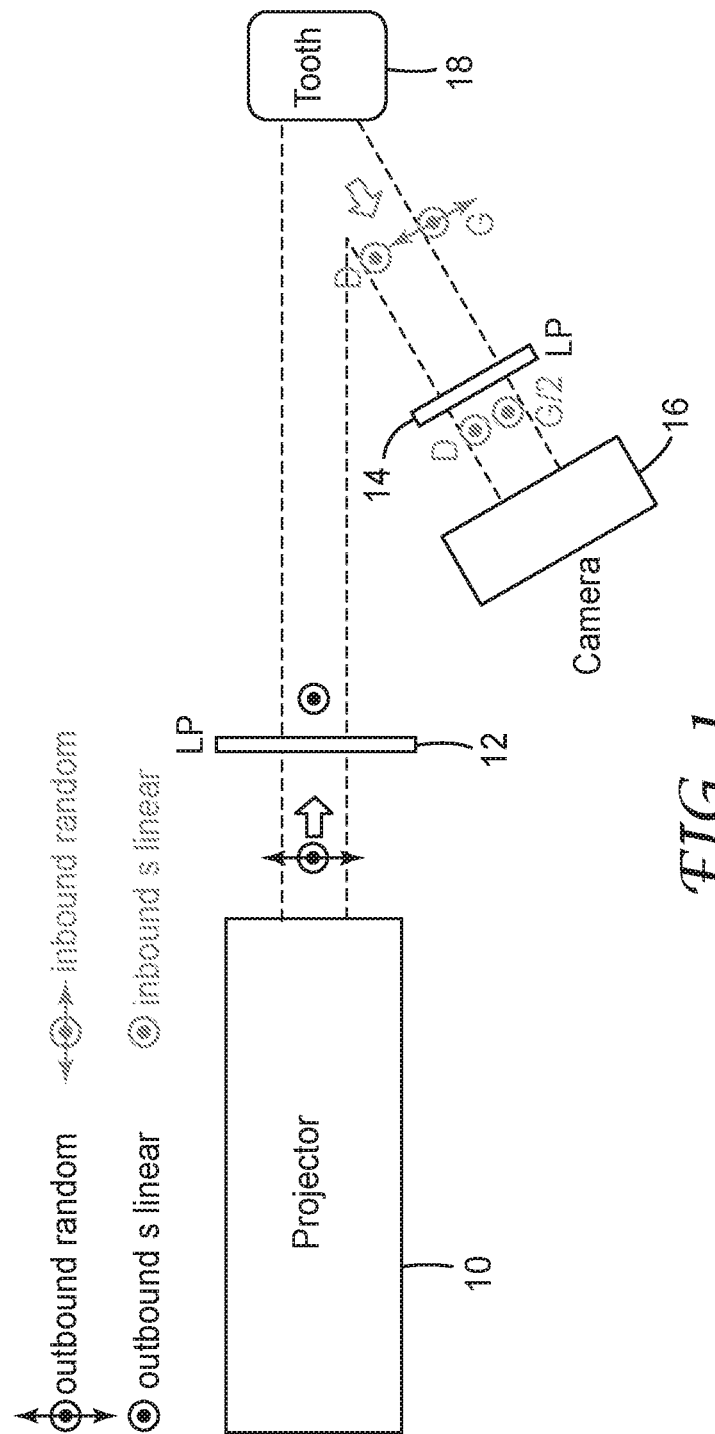
FIG. 1 is an embodiment of an apparatus for projecting a texture pattern for 3D imaging.

FIG. 1 illustrates an embodiment of an apparatus for projecting a texture pattern for 3D imaging. A digital-light-processing (DLP) projector 10 is used to project a texture over the field-of-view and depth-of-field of camera 16. Immediately after exiting the projector, the light is conditioned by a linear polarizer 12. After reflecting and scattering from the object-under-test (for example, tooth 18), the light is filtered by a second linear polarizer 14 that is co-aligned with the first linear polarizer 12. The images are then captured by camera 16. The embodiment shown in FIG. 1 can optionally be implemented without the polarizers 12 and 14.

Figure 2:
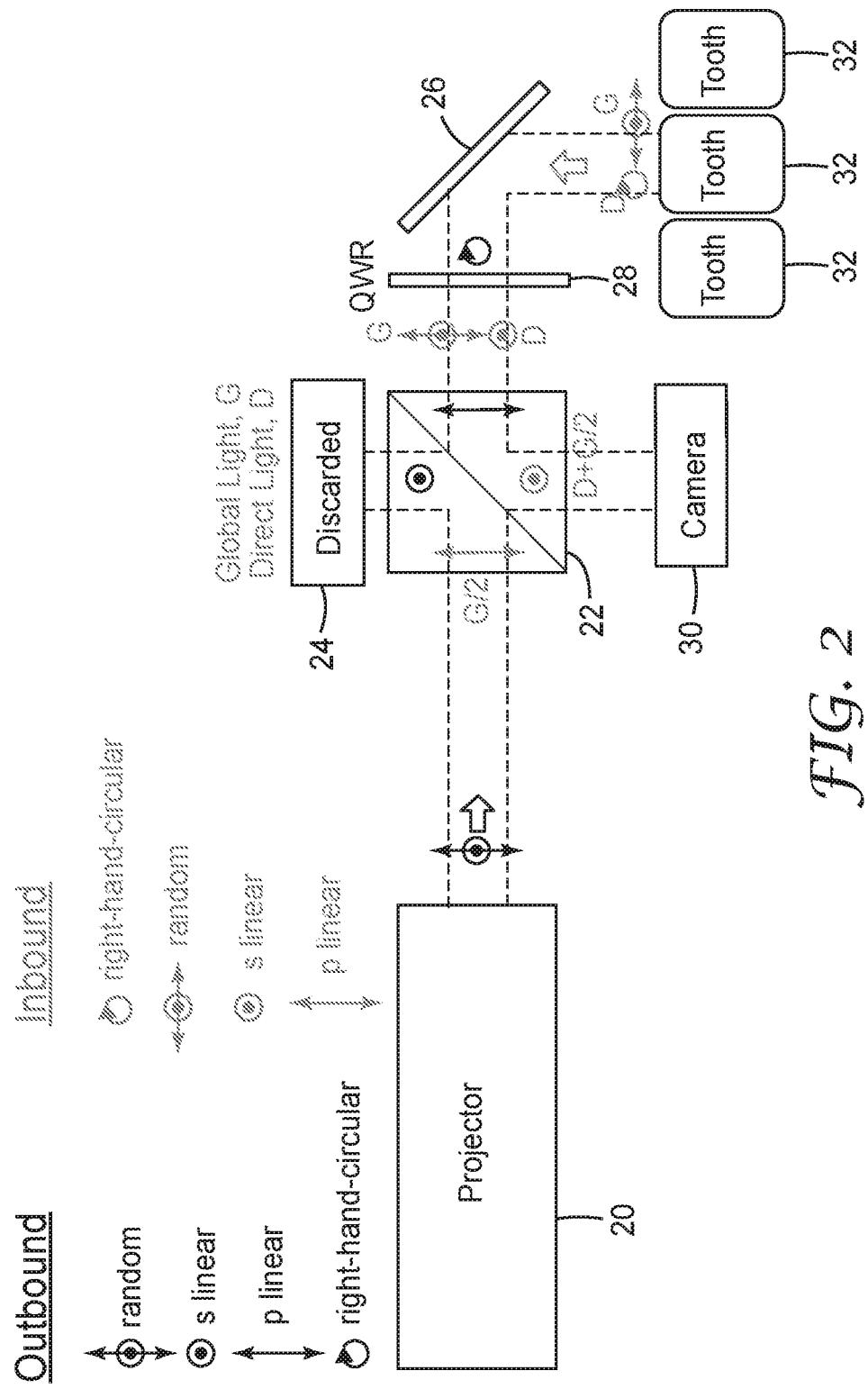
FIG. 2 is another embodiment of an apparatus for projecting a texture pattern for 3D imaging.
Figure 3A:
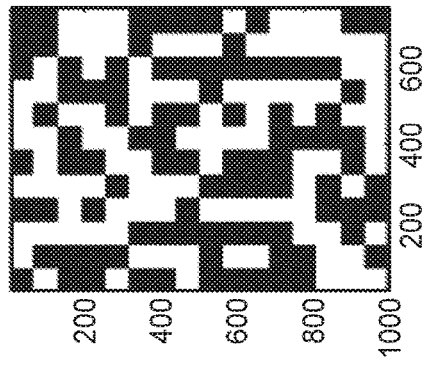
FIGS. 3A-3F are diagrams illustrating examples of texture patterns.
Figure 3B:
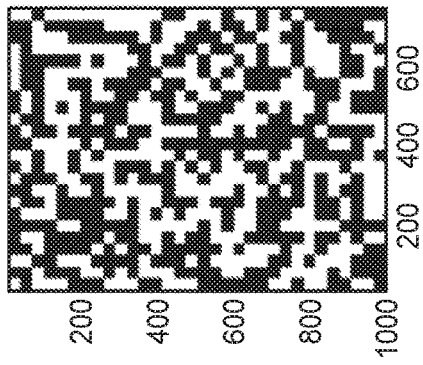
Figure 3C:
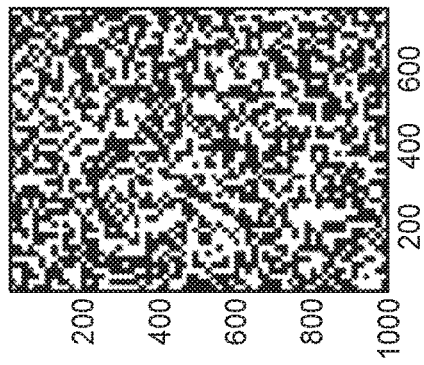
Figure 3D:
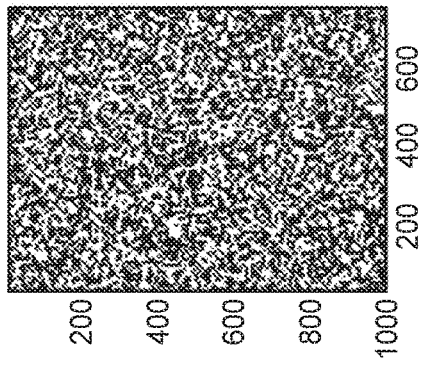
Figure 3E:
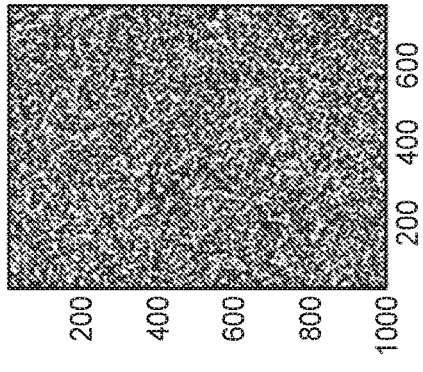
Figure 3F:
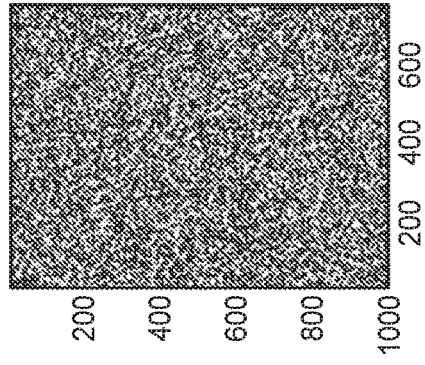

FIG. 2 illustrates another embodiment of an apparatus for projecting a texture pattern for 3D imaging. To make the design compact, the projection axis and camera axis is made common-path by using a polarizing beam-splitter 22. The light exiting a DLP projector 20 is conditioned, which is accomplished by the polarizing beam-splitter 22. The unused linear s-state is reflected within the polarizing beam-splitter 22, upwards and away from the camera 30 where it can be absorbed/discarded as represented by block 24. After exiting the polarizing beam-splitter 22 the linear p-state light passes through a quarter-wave retarder (QWR) 28, after which the light is right-hand circular polarized. The light can be reflected by a mirror 26 onto the teeth 32 to be imaged. When the light directly reflects from the surface of teeth 32, the light is converted to inbound left-hand circular polarization. Passing once again through the QWR 28 converts the light into linear s-state polarization. Within the polarizing beam-splitter 22, the linear s-state reflects towards the camera 30 where images are captured. Any residual inbound linear e-state light will be sent back towards the projector where it is discarded. Polarizing beam-splitter 22 can be implemented with, for example, a polarizing cube beam-splitter (PCBS) or an irregularly shaped polarizing beam-splitter. The embodiment shown in FIG. 2 can optionally be implemented without the QWR 28, in which case the beam-splitter 22 need not be polarizing and could be implemented with, for example, a plate beam-splitter.

The DLP projectors 10 and 20 produce a random texture pattern. Projecting a texture pattern onto a translucent object and then capturing an image of the scene with the camera can be described as follows, $$I = S \cdot P \cdot \text{Texture}, \quad (1)$$

where I is the image frequency spectrum; Texture is the original high contrast pattern; P is the transfer function describing the fidelity of the projector; S is the transfer function of the object surface; and C is the transfer function of the camera. Furthermore, all of the parameters in equation (1) are also functions of spatial frequency and two-dimensional spatial coordinates that are orthogonal to the system axis. In an ideal case, C, S, and P would be unity over the entire spatial-frequency domain and the image would perfectly reproduce the original Texture pattern. However, each of the transfer functions exhibit a decreasing amplitude with respect to frequency, ranging from 1 to zero. The amplitude describes the transferred contrast level at a given spatial frequency, where contrast is the ratio of the difference between the maximum and minimum pixel exposure divided by the sum of the maximum and minimum pixel exposure. In effect, the contrast will decrease as the pattern becomes finer. The camera is governed by its own modulation transfer function (MTF). The surface scatter S can be approximated to resemble a function analogous to the camera MTF. The diffusion approximation permits the tooth to be characterized with an MTF, depending upon its scattering properties, and thus be incorporated into a single MTF that describes the entire imaging system. With a single system MTF, an optimum projected texture pattern can be determined.

The projector optics are the first to exert its own MTF onto the initially pristine Texture pattern. The C and P parameters are direct consequences of the optical design of the camera and projector, respectively, and can be easily modeled from optical raytracing software. On the other hand, S depends upon the type of object under test and will not be known a priori. To maintain a satisfactory contrast level in the images, depending on the S encountered in any particular scene, the characteristics of Texture may need to adapt and not remain static. In other words, it may be likely that there is not a single Texture that is a ubiquitous solution to capturing adequate images for all teeth. A DLP projector can be useful in such circumstances, since the nature of Texture could be rapidly optimized within a few video frames, depending upon feedback gathered from the scene. Although not shown in equation (1), the presence of the polarization filters flanks the S parameter. For the system in FIG. 1, equation (1) can be written as, $$I = C \cdot LP \cdot S \cdot LP \cdot P \cdot \text{Texture}, \quad (2)$$

where the linear polarizers LP have a co-linear alignment. The description for the system in FIG. 2 is similar to equation (2) but with the introduction of the quarter-wave retarder QWR, $$I = C \cdot LP \cdot QWR \cdot S \cdot QWR \cdot LP \cdot P \cdot \text{Texture}. \quad (3)$$

The components LP and QWR are assumed to have no optical wavelength-dependence.

FIGS. 3A-3F show examples of six different two-dimensional white noise patterns. These examples are the pattern files that are sent to the projector, not actual images captured by the camera. The initial pattern has 1024×768 pixels, where each block may correspond with a single pixel or a group of adjacent pixels. An integer value, shown above each pattern, is chosen to assign the integer number of adjacent pixels into a block with dark or bright settings. For example, in FIG. 3A 64×64 pixels are assigned to each two-dimensional block in the pattern, and in FIG. 3C each block in the pattern is comprised of 16×16 pixels.

Each pattern is two-dimensional and not periodic, i.e. not sinusoidal. Rather, the pattern is white-noise meaning that the spatial frequency spectrum possesses signal ranging from DC out to the upper limit dictated by the pattern cut-off frequency, i.e. $f_{max} = 1/(2 \text{ pixels})$. The white noise pattern serves two purposes: it provides image features that permit good feature-correspondence between images of the stereo-vision camera; there is broadband spatial frequency illumination available that permits a measurement of the imaging system modulation transfer function; and it permits the measure of the diffuse reflectance spatial frequency spectrum of parameter S.

The cameras 16 and 30 can be implemented with, for example, a CMOS digital image sensor. The image sensor can be partitioned into multiple regions corresponding with the optical channels of the apparatus as implemented in a multi-view intra-oral scanner. Optionally, multiple image sensors can be used for the channels. Examples of multi-view intra-oral scanners are disclosed in U.S. Pat. No. 9,591,286, which is incorporated herein by reference as if fully set forth.

The DLP projectors can be implemented within an intra-oral scanner containing the apparatus and can be located, for example, behind or adjacent the image sensor with respect to the object to be imaged. The DLP projectors can be controlled via a processor to tune the projected texture pattern before or during imaging, or both before and during. Instead of a projector, the system can use a mask to project the pattern. The systems use multiple channels to the image sensors with co-axial projecting and imaging.

The projected texture patterns, for example those shown FIGS. 3A-3F, can be composed of pixels clustered into blocks with the blocks being turned off and on in a pseudo-random pattern. For example, each block can have a dark (off) or bright (on) setting for the pattern. The translucency of the teeth (or other intra-oral structures) to be imaged can determine a size of the blocks in the pattern. As the surface of the object to be imaged becomes more translucent or transparent, the blocks can become larger for the image sensor to resolve the blocks in the pattern. The pixel size of the blocks can be fine-tuned for optimum performance and can overcome the scarcity of features on the surface of the object to be imaged, or the translucency of such surface, to essentially simulate powder applied to the surface. In particular, the configuration of the blocks, or other projected texture pattern, can be sufficient for the image sensor to resolve features on a surface of the object to be imaged and possibly optimized for the best or a desired resolution of the features by the image sensor.

In the patterns of FIGS. 3A-3F, ideally each adjacent grouping of blocks (configuration of bright and dark blocks) is unique along each horizontal direction with respect to other adjacent grouping of blocks along the same horizontal direction, but not necessarily between different horizontal directions. For example, in FIG. 3D each adjacent grouping of blocks along a horizontal direction has a different pattern (configuration of bright and dark blocks) from each of the other adjacent grouping of blocks along the same horizontal direction. Optionally, some adjacent groups of blocks along the same horizontal direction can have the same pattern. Also, random texture includes pseudo-random texture, since the texture may not be truly random.

The Texture parameter in equation (1) is controlled by the size of the blocks and which blocks are turned on (bright) or turned off (dark). The texture patterns can be stored as a series of files sent to the projector, for example files containing the patterns shown in FIGS. 3A-3F, with each pattern in the series being different from the other patterns in the series. The apparatus can cycle through the files sent to the projector and evaluate the resulting images to find the best pattern for particular objects to be imaged. The other parameters in equation (1), aside from Texture, cannot be directly controlled.

Figure 4:
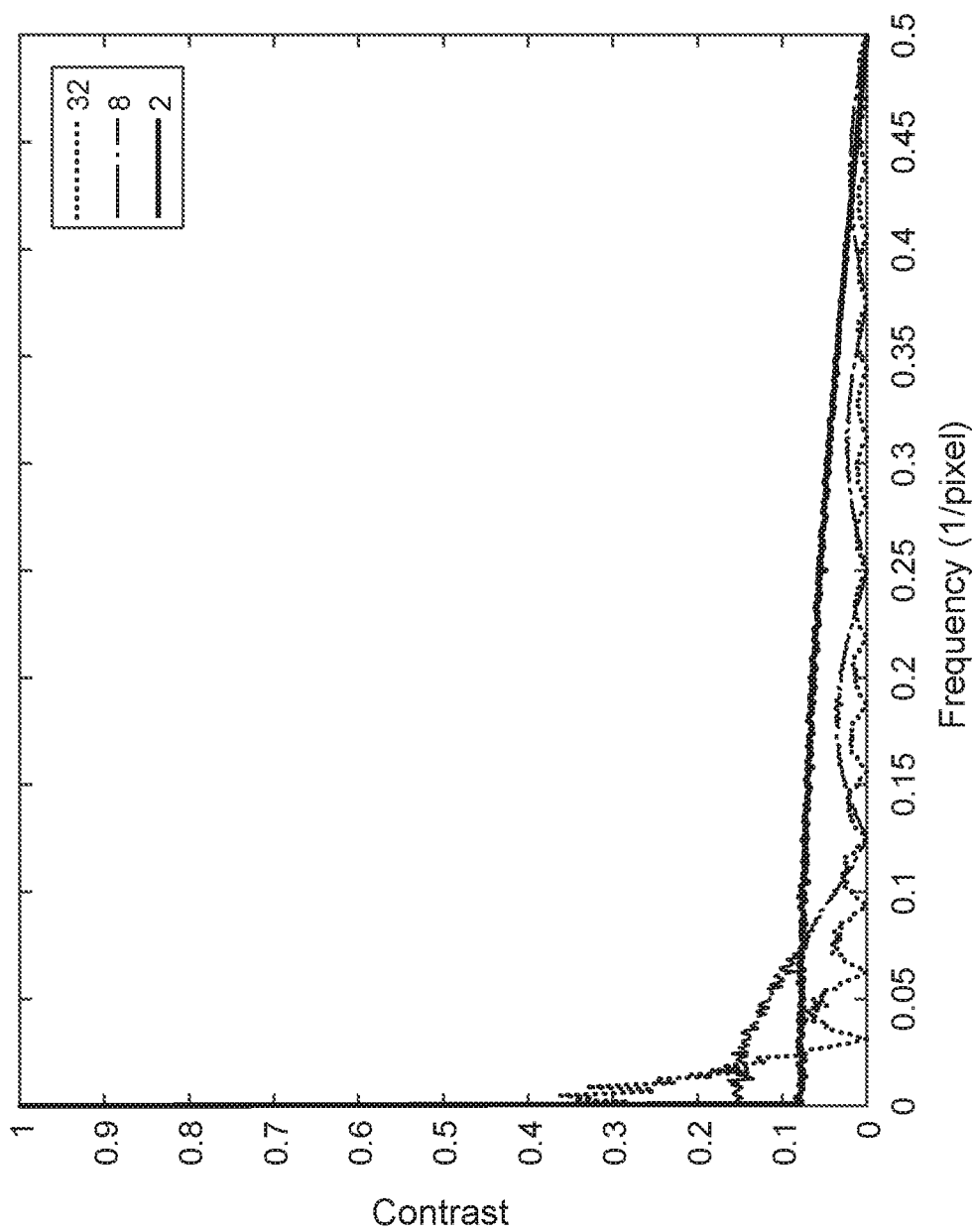
FIG. 4 is a graph of the spatial frequency spectrum of a pseudo-random pattern sent to a projector for block pixel sizes of 2, 8, and 32.

FIG. 4 is a graph of the spatial frequency spectrum of a pseudo-random pattern sent to a projector for block pixel sizes of 2, 8, and 32.

Figure 5:
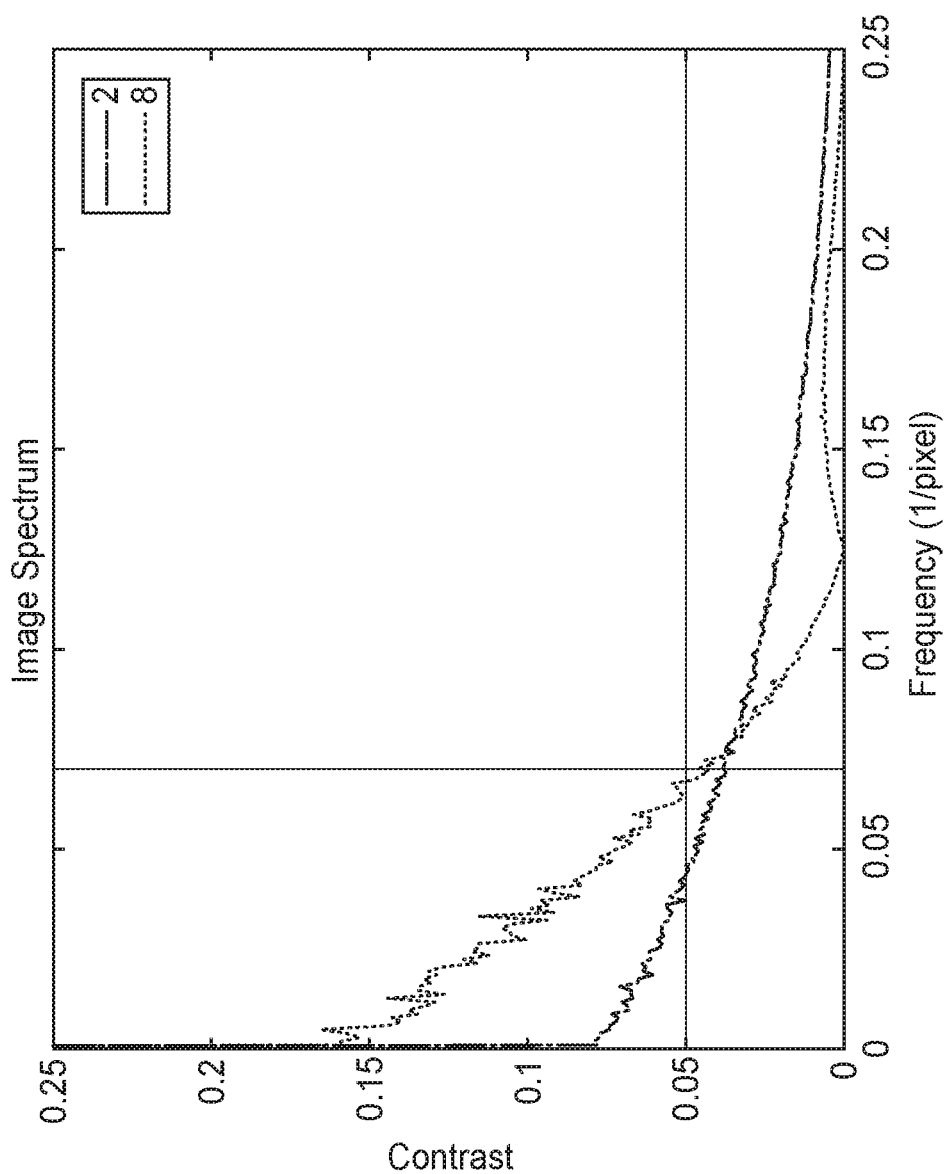
FIG. 5 is a graph of the spatial frequency spectrum of an image after the transfer functions of the projection lens, tooth, and camera have been taken into effect for patterns with block pixel sizes of 2 and 8.

FIG. 5 is a graph of the spatial frequency spectrum of an image after the transfer functions of the projection lens, tooth, and camera have been taken into effect for patterns with block pixel sizes of 2 and 8. The vertical solid line at 0.07/pixels represents a cut-off frequency, the horizontal line at 0.05 represents a noise floor, and both lines are thresholds for adequate stereo-vision depth mapping.

The invention claimed is:

1. An apparatus for intra-oral imaging using a projected texture pattern, comprising:
   a projector; and
   an image sensor,
   wherein the projector is configured to determine a size of blocks for a random texture pattern based on translucency of an object to be imaged and project the random texture pattern of light to the object to be imaged, and the image sensor is configured to receive the projected texture pattern from the object to be imaged, and wherein the size of blocks included in the projected texture pattern is sufficient for the image sensor to resolve features on a surface of the object to be imaged.

2. The apparatus of claim 1, further comprising:
   a first linear polarizer located between the projector and the object to be imaged; and
   a second linear polarizer arranged co-linear with the first linear polarizer and located between the image sensor and the object to be imaged,
   wherein the projector is configured to project the random texture pattern of light through the first linear polarizer, and the image sensor is configured to receive the projected texture pattern through the second linear polarizer.

3. The apparatus of claim 1, wherein the projector is configured to project the texture pattern along multiple optical channels, and the image sensor is configured to receive the projected texture pattern from the multiple optical channels.

4. The apparatus of claim 1, wherein the projector comprises a digital-light-processing projector.

5. The apparatus of claim 1, wherein the texture pattern is a two-dimensional pseudo-random pattern of pixels.

6. The apparatus of claim 1, wherein the texture pattern is two-dimensional and is comprised of an integer value of pixels clustered into blocks, wherein each block has a dark or a bright setting.

7. The apparatus of claim 6, wherein each adjacent group of blocks in a row of the texture pattern has a unique configuration of dark and bright blocks with respect to other adjacent groups of blocks in the row.

8. The apparatus of claim 6, wherein the texture pattern is not periodic.

9. The apparatus of claim 1, wherein the projector is configured to project a series of random texture patterns of light to the object to be imaged, and the image sensor is configured to receive the series of projected texture patterns from the object to be imaged, wherein each pattern in the series is different from other patterns in the series.

10. An apparatus for intra-oral imaging using a projected texture pattern, comprising:
    a projector;
    a beam-splitter located between the projector and an object to be imaged; and
    an image sensor,
    wherein the projector is configured to determine a size of blocks for a random texture pattern based on translucency of the object to be imaged and project the random texture pattern of light through the beam-splitter to the object to be imaged, and the image sensor is configured to receive the projected texture pattern from the object to be imaged through the beam-splitter, and wherein the size of blocks included in the projected texture pattern is sufficient for the image sensor to resolve features on a surface of the object to be imaged.

11. The apparatus of claim 10, further comprising a quarter-wave retarder located between the beam-splitter and the object to be imaged, wherein the beam-splitter is polarizing, and the projector is configured to project the random texture pattern of light through the quarter-wave retarder.

12. The apparatus of claim 11, further comprising a mirror located between the quarter-wave retarder and the object to be imaged for directing the projected texture pattern to the object to be imaged.

13. The apparatus of claim 10, wherein the projector is configured to project the texture pattern along multiple optical channels, and the image sensor is configured to receive the projected texture pattern from the multiple optical channels.

14. The apparatus of claim 10, wherein the projector comprises a digital-light-processing projector.

15. The apparatus of claim 10, wherein the texture pattern is a two-dimensional pseudo-random pattern of pixels.

16. The apparatus of claim 10, wherein the texture pattern is two-dimensional and has blocks comprised of an integer number of pixels, wherein each block has a dark or a bright setting.

17. The apparatus of claim 16, wherein each adjacent group of blocks in a row of the texture pattern has a unique configuration of dark and bright blocks with respect to other adjacent groups of blocks in the row.

18. The apparatus of claim 16, wherein the texture pattern is not periodic.

19. The apparatus of claim 10, wherein the projector is configured to project a series of random texture patterns of light to the object to be imaged, and the image sensor is configured to receive the series of projected texture patterns from the object to be imaged, wherein each pattern in the series is different from other patterns in the series.

20. An apparatus for intra-oral imaging using a projected texture pattern, comprising:
    a projector;
    a polarizing beam-splitter located between the projector and an object to be imaged;

a quarter-wave retarder located between the beam-splitter and the object to be imaged; and an image sensor, wherein the projector is configured to determine a size of blocks for a random texture pattern based on translucency of the object to be imaged and project the random texture pattern of light through the beam-splitter and quarter-wave retarder to the object to be imaged, and the image sensor is configured to receive the projected texture pattern from the object to be imaged through the beam-splitter, wherein the texture pattern is two-dimensional and has blocks comprised of an integer number of pixels, each block has a dark or a bright setting, and each adjacent group of blocks in a row of the texture pattern has a unique configuration of dark and bright blocks with respect to other adjacent groups of blocks in the row.

* * * * *